Figure 1:
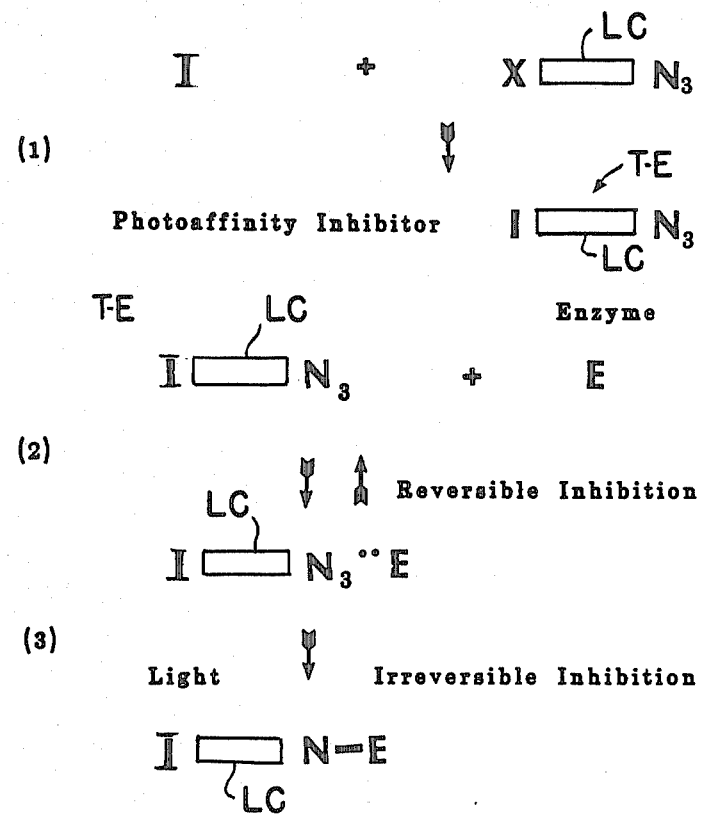

United States Patent [19]

Cohen

[11] Patent Number: 4,771,130

[45] Date of Patent: Sep. 13, 1988

[54] TARGET-ENTRAPPED DRUGS

[76] Inventor: William Cohen, 1430 Tulane Ave., Tulane University, New Orleans, La. 70112

[21] Appl. No.: 581,413

[22] Filed: Feb. 17, 1984

[51] Int. Cl.$^4$ ............... A61K 41/00; C07H 15/00; C07H 17/00

[52] U.S. Cl. .................................... 536/8; 514/866; 514/912; 514/913; 514/914; 604/20

[58] Field of Search .................. 536/8; 514/25, 866, 514/912, 913, 914

[56] References Cited

U.S. PATENT DOCUMENTS

| | | | |
|---|---|---|---|
| 3,346,559 | 10/1967 | Berlin | 536/8 |
| 4,021,546 | 5/1977 | Bodor | 514/26 |
| 4,263,428 | 4/1981 | Apple et al. | 536/6.4 |
| 4,328,204 | 5/1982 | Wasserman et al. | 514/182 |
| 4,419,348 | 12/1983 | Rahman et al. | 536/5 |
| 4,474,751 | 10/1984 | Haslam et al. | 514/45 |
| 4,474,753 | 10/1984 | Haslam et al. | 514/54 |
| 4,478,822 | 10/1984 | Haslam et al. | 514/54 |
| 4,496,548 | 1/1985 | Moldowan et al. | 536/8 |
| 4,671,958 | 6/1987 | Rodwell et al. | 424/85 |

OTHER PUBLICATIONS

Varma et al., "Chem. Abst.", vol. 86, 1977, p. 69563d.
Megaw et al., "Chem. Abst.", vol. 101, 1984, p. 43524v.

*Primary Examiner*—Ronald W. Griffin
*Attorney, Agent, or Firm*—Cushman, Darby & Cushman

[57] ABSTRACT

A target-entrapped drug comprising three chemically joined components
(1) the active drug component;
(2) a linking chain; and
(3) an activatable group;

the activatable group on exposure of the drug to activation liberating components (1) and (2) so that the drug component (1) is bound to a selected target site through the linking chain (2). The drug is administered and then activated by exposure to electromagnetic radiation or other energy such as thermal energy at the anatomic target site.

6 Claims, 8 Drawing Sheets

A-SUB-Q

Synthesis of A-SUB-Q

Spectra of A-SUB-Q ± Photolysis

DIFFERENTIAL SPECTRA of A-SUB-Q ± PHOTOLYSIS $K_i$ of A-SUB-Q

PHOTO-INHIBITION OF ALDOSE REDUCTASE

X-RAY-INHIBITION OF ALDOSE REDUCTASE

INHIBITION BY IMMOBILIZED A-SUB-Q

INHIBITION OF A.R. BY A-SUB-Q INHIBITED A.R.

INHIBITION OF A.R. BY A-SUB-Q INHIBITED A.R.

TARGET-ENTRAPPED DRUGS

The present invention relates to novel drugs and their use in treating diseases or disorders. The invention is particularly concerned with the provision of a special type of drug which is effective in irreversibly inhibiting the enzyme aldose reductase in the eye and which is, therefore, useful in treating diabetic cataracts or related eye problems which may be caused by aldose reductase. However, as will be evident from the description which follows, the invention is of broader application in relating to what may be termed "target-entrapped" drugs.

Target-entrapped drugs (hereinafter referred to as "T-E" drugs) constitute, according to the invention, a new class of drugs whose effectiveness is potentiated at a specific anatomic site by a variety of techniques, such as electromagnetic irradiation of that site or treating with any other energy such as thermal energy, so as to produce a tight or irreversible drug-receptor bond, e.g. a covalent bond.

In the conventional use of a typical drug, the drug rapidly equilibrates throughout the body soon after administration, reversibly binds to its specific receptor site and produces its pharmacological effect. The effectiveness of such drug increases to a maximum, then falls to zero as the drug is detoxified and excreted from the system, usually over a period of hours. In contrast, a T-E drug, according to the invention, differs in that, after administration, if one appropriately irradiates or otherwise appropriately energizes a selected specific anatomical target site when the pharmacological effect of the drug is at a maximum, a tight or irreversible drug-receptor bond is produced. This prevents detoxification and excretion of the drug from that specific targeted site and thus prevents a decrease of pharmacological effect. Upon irradiation, a reversible drug-receptor interaction is caused to change into a tight or irreversible drug-receptor interaction. Consequently, the half-life of effectiveness for a T-E drug is the biological turnover time of the drug-receptor complex or neosynthesis of the receptor in contrast to that for a typical conventional drug whose half-life is a function of the rate of detoxification and excretion of the drug.

The selected target site may be a specific receptor, such as an enzyme, in a specific organ, such as the kidney. The same receptor may be present in many organs, but if the target organ alone is irradiated, then the drug will function for a prolonged period only in that organ thereby eliminating potential complications and side-effects as a result of repeated administration of the drug. Since they will generally function by covalently binding to receptor sites, smaller doses of T-E drugs will be needed because lesser amounts will serve to achieve and retain therapeutic levels. In addition, if a drug produces undesirable side-effects at a therapeutic dose level, several still smaller doses may be administered over a relatively short time so that a cumulative effective dose will be attained in the irradiated specific target site area.

The electromagnetic irradiation employed to initiate the covalent coupling of T-E drug to receptor site can be of any type such as visible light, ultra-violet light, and X-rays. The anatomic target site can be as large or small as desired and is limited only by the nature of the electromagnetic radiation used, the equipment available and the techniques of irradiation.

A second action of T-E drugs is the formation of soluble-immobilized or membrane-immobilized drugs. Although a T-E drug may have extremely high affinity for its receptor site, some of the drug present in the anatomic target site will not be bound to receptor sites. Upon irradiation, these molecules of T-E drug will react non-specifically. Some of the T-E drug will bond to extra- or intra-cellular membrane surfaces; some will bond to soluble proteins (e.g. a soluble-immobilized drug) in the cytoplasm or subcellular organelle of cells. This non-specifically bound (e.g. covalently bound) T-E drug will retain its ability to reversibly bind to receptor sites and produce its physiological response. In either case, this drug, too, will be retained in the target area and will be long acting because it will not diffuse out or be detoxified by normal detoxification processes. The drug action by the membrane-bound and soluble-immobilized drug will simply be added to the specific T-E drug action. The overall contribution of non-specifically bound drug can vary from insignificant to highly significant.

As will be appreciated from the foregoing, the principal object of the present invention is to provide a novel drug design concept such that drug therapy may be directed to a specific anatomical site and retain its effectiveness over an extended period of time. Another object of the invention is to provide a T-E drug that will irreversibly bind to a selected receptor site or sites to give the results and advantages generally referred to above. A more specific object is to provide a drug composition which can be used to irreversibly inhibit the enzyme aldose reductase in a selected target organ, e.g. an eye or eye lens. Another specific object of the invention is to provide a T-E drug for effectively dealing with diabetic cataracts and related eye diseases. Other objects, all based on the concept of providing a T-E drug that will tightly or irreversibly bind to the drug receptor site in the anatomic target site, will also be hereinafter apparent.

Broadly stated, the T-E drug of the invention comprises a chemical combination of three components (1) a therapeutically active component or drug portion, e.g. an aldose reductase inhibitor segment; (2) a linking component intended to bind the drug portion to the target site; and (3) a portion activatable by an energy source such as electromagnetic radiation, e.g. an azide component which is light sensitive or X-ray sensitive and which, on exposure to light or X-ray when the T-E drug is located at the desired target site, liberates the combination of (1) and (2) for binding to the site to irreversibly effect the desired therapeutic result.

It will be appreciated that a wide variety of drugs may be designed using the concept broadly described above. Thus, while the invention is hereinafter exemplified by reference to the preparation of a specific compound which is called "Asub-Q" for convenience, and its use as a T-E drug for binding to the enzyme aldose reductase, it will be recognized that the invention is of much broader scope.

It is known that various medical problems are caused by the enzyme aldose reductase. For example, it is presently believed that diabetic complications, such as cataract formation, retinopathy, neuropathy and others are the result of the high production of sorbitol by aldose reductase. In the case of diabetic cataracts, it appears that the enzyme aldose reductase rapidly catalyzes the reduction of glucose to sorbitol in diabetics whose blood glucose is at higher than normal concentrations. Sorbitol cannot be rapidly metabolized nor can it rapidly diffuse out of the lens. Thus, there is a tendency for its concentration to increase. As this occurs, osmotic pressure in the lens increases inducing water to be absorbed and swelling of the lens to occur. This swelling of the lens promotes changes such as in protein conformation which results in opacity of the lens, i.e. cataract formation.

It will be appreciated from the foregoing that the inhibition of aldose reductase in diabetics should be useful in preventing diabetic cataracts and various related diabetic complications (Fagius and Jameson, J. Neur, Neurosurg, and Psych 44, 991–1001 (1981); Robinson et al. Sci 222, 1177–1779 (1983); Chem & Eng. News, Sept. 5, 1983, p. 5). The product herein called "Asub-Q", which is representative of the invention, is photo or X-ray activatable to irreversibly and effectively bind to aldose reductase. As a consequence, this product should be useful to prevent the formation of diabetic cataracts. It is also believed that, in view of its demonstrated irreversible aldose reductase inhibiting activity, Asub-Q should be more effective than simple reversible aldose reductase inhibitors such as quercitrin or sorbanil in preventing diabetic retinopathy and diabetic neuropathy that occur in tissues other than lens. Additionally, since many humans with senile cataracts are hyperglycemic, it appears that these cataracts may be similar to diabetic cataract and should also be effectively treated with an aldose reductase inhibitor such as Asub-Q.

The invention is more specifically described by reference to the accompanying drawings, a preferred design of T-E drug, according to the invention, being shown in FIG. 1. As there shown, (I) represents the drug component, e.g. an inhibitor, which by itself is only capable of acting reversibly, i.e. it only reversibly binds to a receptor site. The drug portion (I) is reacted, as shown at (1) with a bifunctional reagent which comprises an electromagnetic radiation-sensitive or activatable group $N_3$ (e.g. an azide group) and a convenient reactive group (X), e.g. halogen joined together by a linking component (LC). On reacting (I) and the bifunctional reagent through the reactive group (X), the T-E drug is obtained as a product as shown in FIG. 1. This drug functions to reversibly inhibit an enzyme (E) (or other receptor) as shown in (2) until the T-E drug is subjected to light (or other electromagnetic activating means) as shown at (3). This then liberates the azide or other activatable group ($N_3$) to provide irreversible inhibition by binding the enzyme (E) to the inhibitor (I) through the connecting chain (LC).

As will be evident, the photosensitive irreversible inhibitor or T-E drug contemplated herein comprises three components which are chemically combined, i.e. the inhibitor component I, the component $N_3$ activatable by electromagnetic radiation and the linking component LC. It will be appreciated that the inhibitor component is selected to deal with the particular enzyme or other receptor of concern. A photosensitive azide component $N_3$ is a preferred activatable group although other activatable groups may be used to replace the $N_3$ depending on the nature of the desired external activating means.

The linking component (LC) may also be varied, its essential characteristic being that, on removal of the activatable group (e.g. azide) by exposure to light (or otherwise) at the desired site, it is capable of binding the inhibitor to the enzyme or other receptor site.

Figure 3:
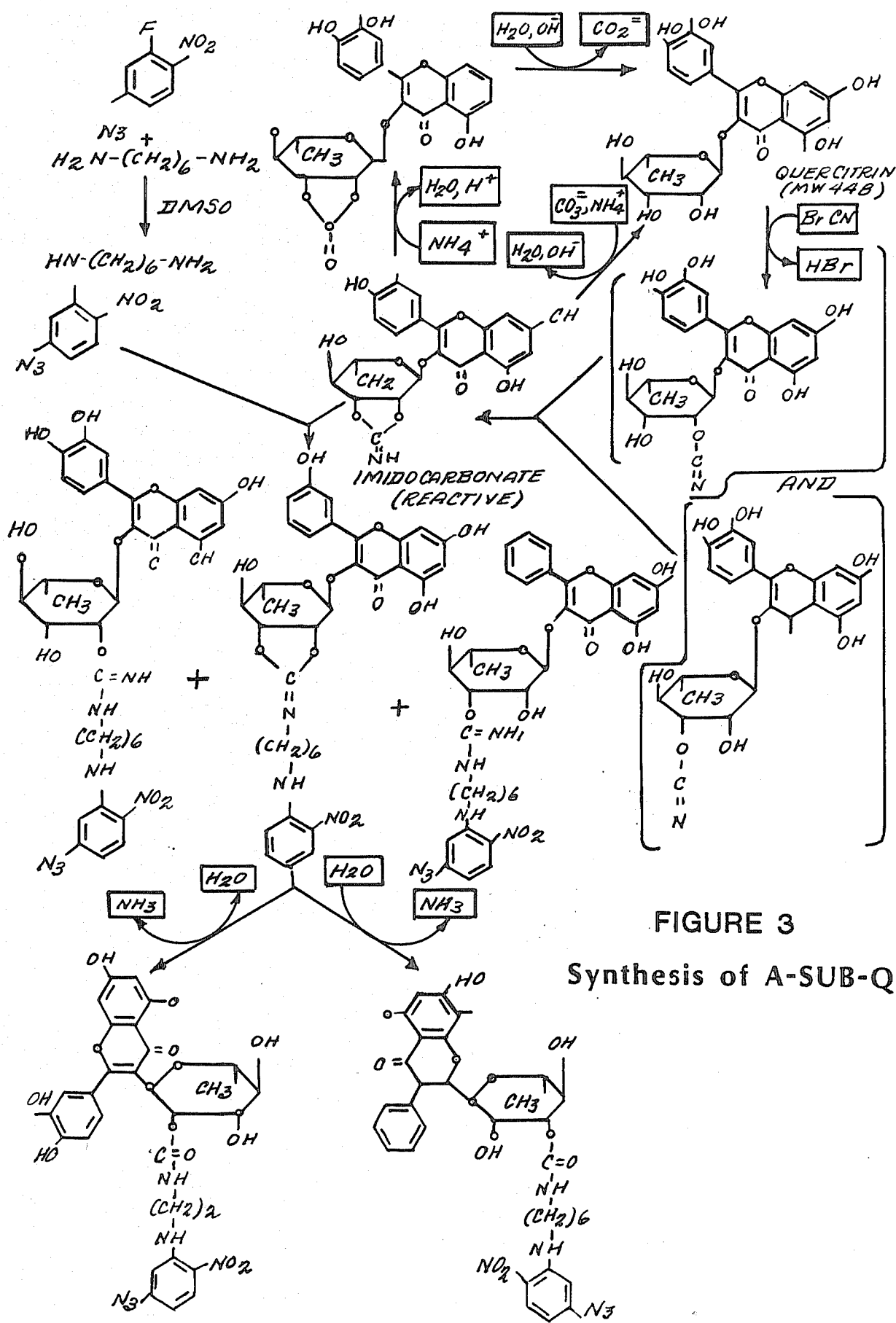

As indicated earlier, a preferred T-E drug according to the invention is Asub-Q which may also be called "NAP-Hex-quercitrin" the latter being derived from the compound's chemical name, i.e. N-(2-nitro-4-azidophenyl) hexylenediamine-N-(2'-O-quercitrin) and isomers such as those shown in FIG. 3. These are representative of a general class of photosensitive azide-substituted quercitrins which can be used to irreversibly inhibit aldose reductase.

Figure 2:
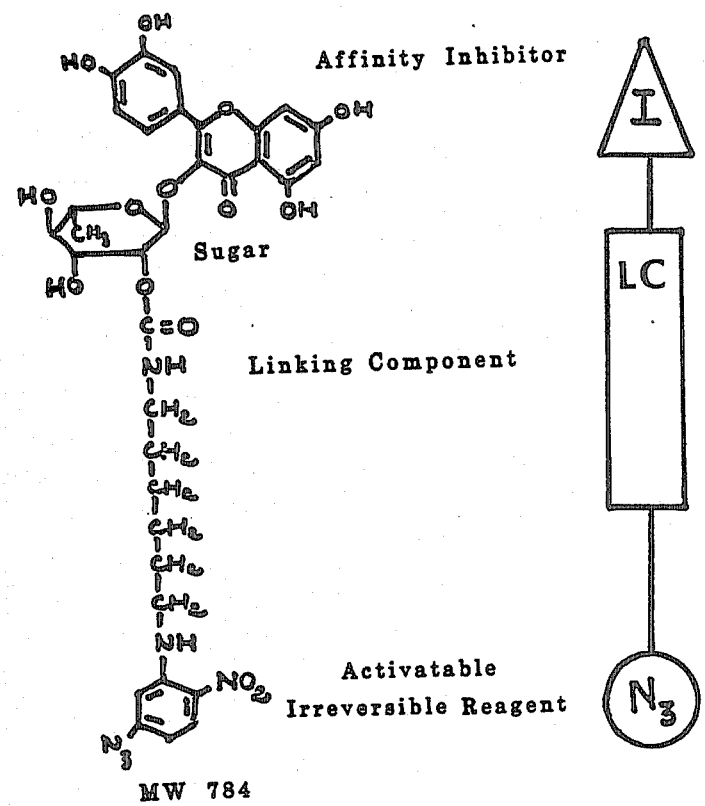

The chemical structure of Asub-Q (or NAP-Hex-quercitrin) is shown in FIG. 2. As will be evident, the product consists of three chemically bound component units, i.e. quercitrin which is the reversible inhibitor (I) of aldose reductase, the photosensitive nitrophenylazide component ($N_3$) and the spacer unit (LC) derived from hexamethylene diamine, the unit (LC) chemically binding together component (I) and ($N_3$). On activation by light or X-ray, $N_2$ from the $N_3$ radical of Asub-Q is liberated to leave a site for covalent binding of the quercitrin inhibitor component via the nitrophenyl moiety linked to the polymethylene diamine spacer to the aldose reductase to irreversibly and selectively inhibit the latter's activity.

While Asub-Q includes the hexamethylene diamine spacer unit (LC), it will be appreciated that the nature of this component may be varied. However, it appears essential for optimum binding to use a spacer chain length of greater than 2 or 3 carbons. A polymethylene group of 5–6 carbon atoms appears to be preferable for best effects although somewhat longer chain lengths may be used. Desirably the spacer unit is terminated at each end with an amino group although it is possible that other terminal substituents, and even substitution on the polymethylene chain, could function satisfactorily provided such substitution does not interfere with the inhibiting effect of the inhibitor component (I).

The invention is illustrated by the following examples:

EXAMPLE 1

This example illustrates the preparation of Asub-Q (or NAP-Hex-quercitrin).

(a) Synthesis of NAP-HEX-AMINE

N-(2-nitro-4-azidophenyl)hexylenediamine (NAP-Hex-Amine) was synthesized by a modification of the methods of Rogers and Ladunski (see Biochem 18, 135–140 (1979)) and of Darfler and Marinetti (see Biochem Biophys. Res. Comm 79, 1–7 (1977)), then purified.

All operations carried out with azide compounds were performed under red light. 1.0 gm of 4-fluoro-3-nitrophenyl azide (5.5 mmoles) (FNPA) was gently stirred with 6.4 gm of 1,6-hexylenediamine (55 mmoles) in 10 ml of freshly distilled dimethylsulphoxide (DMSO) under nitrogen at 50° C. for 30 minutes. The product was recovered from the solution by lyophilization.

The resulting crude NAP-Hex-Amine (150 mg) was dissolved in 4 ml of solvent (benzene/methanol/acetic acid, 70:15:15) and purified on a solvent-washed Bio-Sil A, 200–325 mesh, column (2.5×10.0 cm) by elution with the same solvent. The pure product was isolated by lyophilization of the peak fractions. Yield was 68%.

(b) Activation of Quercitrin

Activation of quercitrin was performed in an ice bath using a closed stirred system. Nitrogen, bubbled through the system, was released through a mineral oil trap. Quercitrin (0.5 mmoles) was added to 5 ml of 3N sodium hydroxide solution. This was followed by the dropwise addition of 1.0 ml of BrCN (1.0 gm). The pH was monitored and 3N sodium hydroxide was added to maintain pH 10.5-11.5. Fifteen minutes after acid production ceased, any remaining unreacted BrCN was removed by extraction with ether three times.

(c) Coupling NAP-HEX-AMINE to Activated Quercitrin

The freshly activated quercitrin was added to NAP-Hex-Amine (0.5 mmoles) dissolved in 8 ml DMSO at room temperature and maintained at pH 11.0-11.5 by addition of 3N sodium hydroxide under a nitrogen atmosphere. After 4 hours, the solution was acidified, using 3N HCl, to pH 5.0 and put in the cold for 2 hours. The precipitate was collected on a Buchner funnel, redissolved in fresh solvent, and then dried by flash evaporation at 50° C. The crude product was purified chromatographically using the same system as described above in (a). Thin layer analysis with HPTLC silica gel 60 plates using benzene/methanol/acetic acid (70:15:15) as solvent showed one major spot and two minor spots with Rf values of 0.60, 0.53 and 0.70, respectively. The three spots are isomers and each was found to inhibit aldose reductase reversibly. However, when photolyzed, the isomers inhibited the aldose reductase irreversibly. Yield was 46%.

The synthesis described above is summarized in FIG. 3 which shows the preparation of NAP-Hex-Amine, the activation of quercitrin and its coupling to NAP-Hex-Amine yielding three isomers, respectively.

(d) Spectral Analysis of Asub-Q

Figure 4:
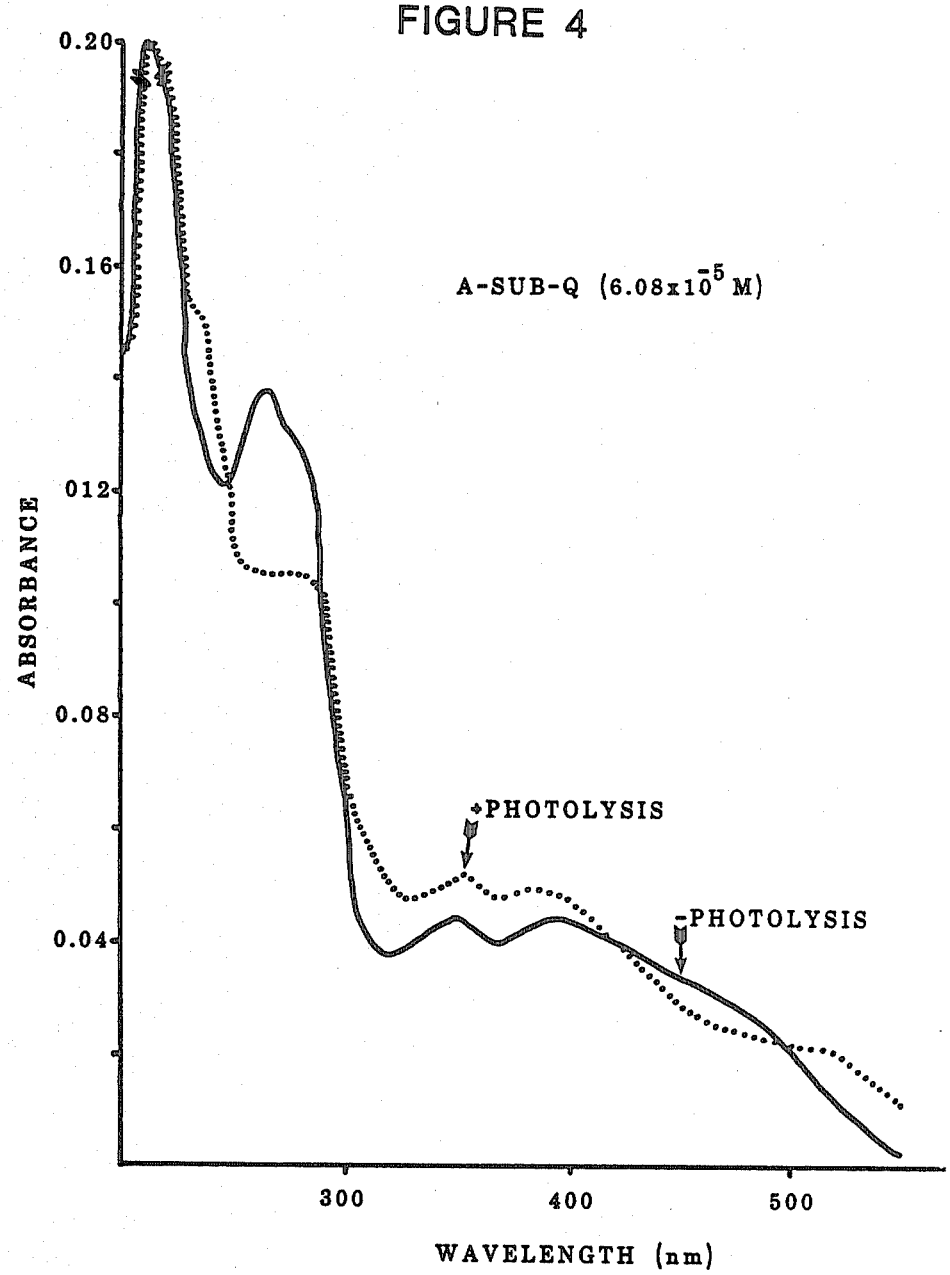
Figure 5:
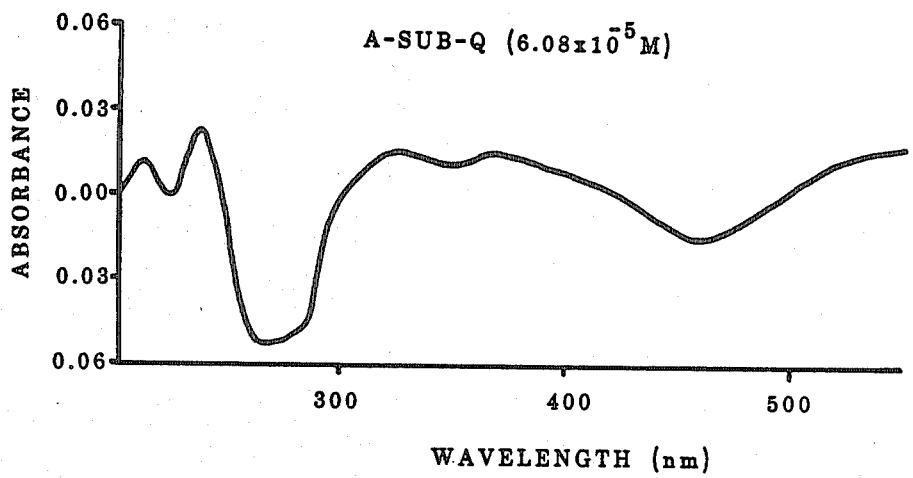

FIG. 4 shows the UV-Visible spectrum before and after 20 minutes of photolysis in a Rayonet Photochemical Reactor with a light source having maximum at 350 nM. The differential spectra is seen in FIG. 5. The decrease in absorbance at 262 nm and 462 mm and the increase in absorbance at 325 nm and 365 nm upon photolysis can be easily seen by eye particularly on thin layer plates. The different extinction coefficients are −855, −247, 263 and 263, respectively.

EXAMPLE 2

This example illustrates the synthesis of gamma-globulin NAP-Hex-quercitrin.

200 mg of bovine g-globulin were dissolved in 2 ml of 0.1M sodium phosphate buffer, pH 6.3 by gently stirring for 30 minutes at room temperature. After 0.2 ml of NAP-Hex-Quercitrin (0.9 mg) was added to the solution, it was split into two fractions, one was photolyzed for 10 minutes while the other was kept in the dark. The adduct was separated from the inhibitor solution by passing through a Sephadex G-25 column (0.7×7.0 cm, 0.5 ml/minute). The purple protein elutes at the void volume cleanly separated from the inhibitor. Prior photolysis of the protein alone or the inhibitor alone had no effect on its elution whether run alone or together on the column. In the control, the colorless protein was also cleanly separated from the inhibitor. When a BioRad P-15 column was used in place of the Sephadex column the results were the same. Exhaustive dialysis against buffer did not separate the inhibitor from the protein. It was concluded from this that the inhibitor was covalently linked to the g-globulin.

EXAMPLE 3

This example illustrates the inhibition of aldose reductase by Asub-Q.

(a) REVERSIBLE INHIBITION

Tests to determine the inhibiting activity of Asub-Q against aldose reductase indicate that Asub-Q reversibly inhibits aldose reductase in a crude extract of rat lens with a Ki (the binding constant representative of the inhibiting activity of a compound) similar to quercitrin itself.

Lens aldose reductase used for test purposes was extracted and assayed by the technique reported by Hayman and Kinoshita (see J.Biol. Chem. 240, 877–882 (1965)). The extract was usually adjusted to pH 7.0 and lyophilized. This product is stable indefinitely in the cold and provides particularly reliable assay results since day to day rates are reproducible.

Figure 6:
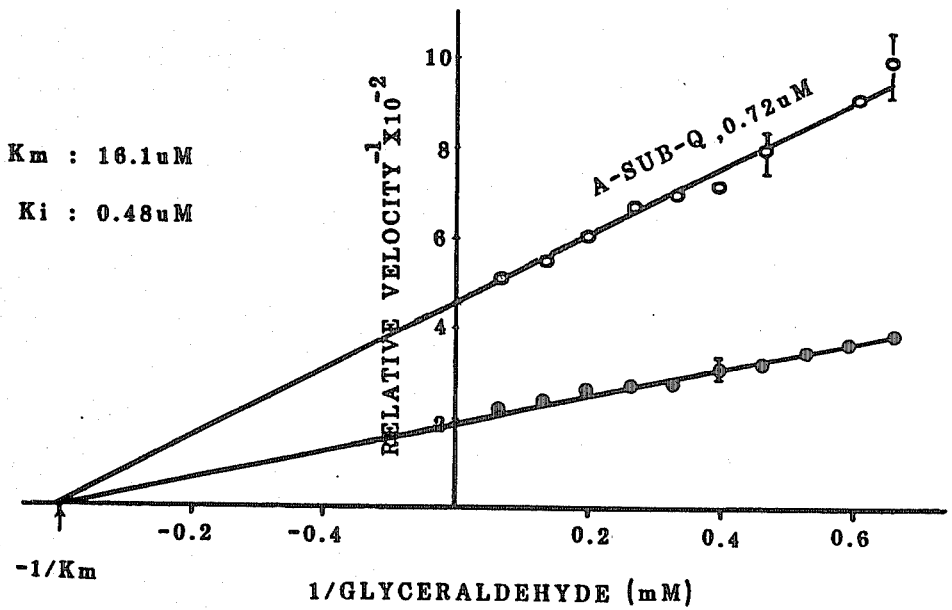

The Ki and type of inhibition of aldose reductase by Asub-Q (0.274 mM) was determined at pH 6.3 in 0.1M phosphate buffer using a saturating concentration of NADPH (121 uM). The results are plotted in FIG. 6. Asub-Q was found to be a noncompetitive inhibitor with a Ki of 0.48 uM, very similar to quercitrin.

(b) IRREVERSIBLE-INHIBITION INDUCED BY PHOTOIRRADIATION

When the mixture of Asub-Q and extract is irradiated with light (maximum at 350 nM) followed by chromatographic removal of small molecules, it is found that the enzyme is inhibited. Kinetic analysis shows that both specific irreversible inhibition and non-specifically bound reversible (soluble immobilized inhibitor) inhibition occur.

Figure 7:
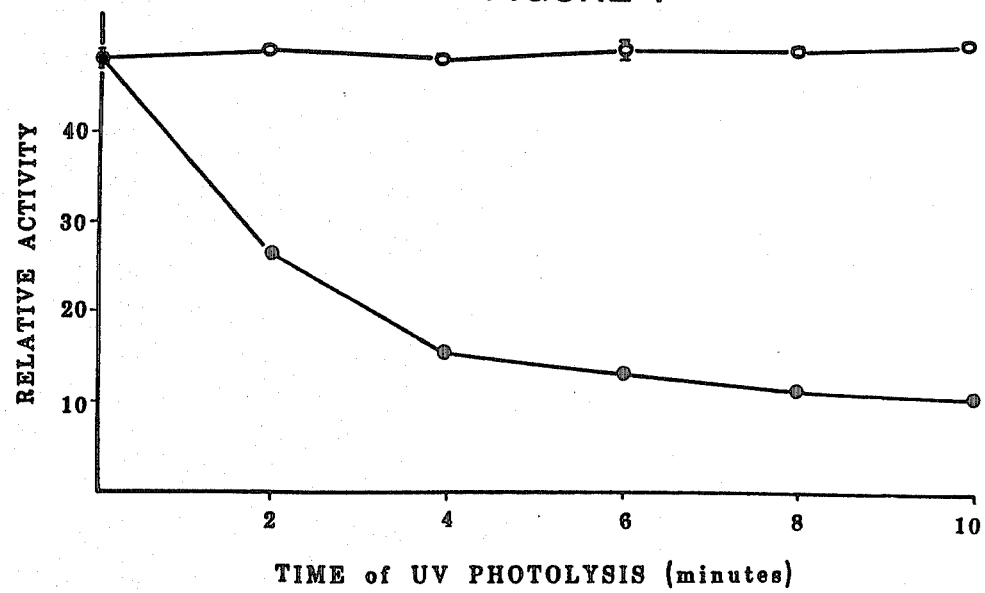

Photolysis of Asub-Q and aldose reductase was studied in the presence and absence of saturating substrate concentrations (0.274 mM glyceraldehyde, and 0.111 mM NADPH) in 0.1M phosphate buffer, pH 6.3. Photolysis was performed in 3 ml quartz spectrophotometer cuvettes in a Rayonet photochemical reactor with a 350 nm maxima light source. The enzyme was separated from the non-covalently bound inhibitor by passing the photolyzed solution through a Sephadex G-25 column as described above. The results are plotted in FIG. 7. The results show that aldose reductase with no inhibitor present was not affected by the photolysis. The enzyme photolyzed with inhibitor in the presence or absence of substrate is 80% inhibited after 10 minutes. It was found that irreversible inhibition is quite rapid, roughly 40% in one minute.

(c) IRREVERSIBLE INHIBITION INDUCED BY X-RAY IRRADIATION

Figure 8:
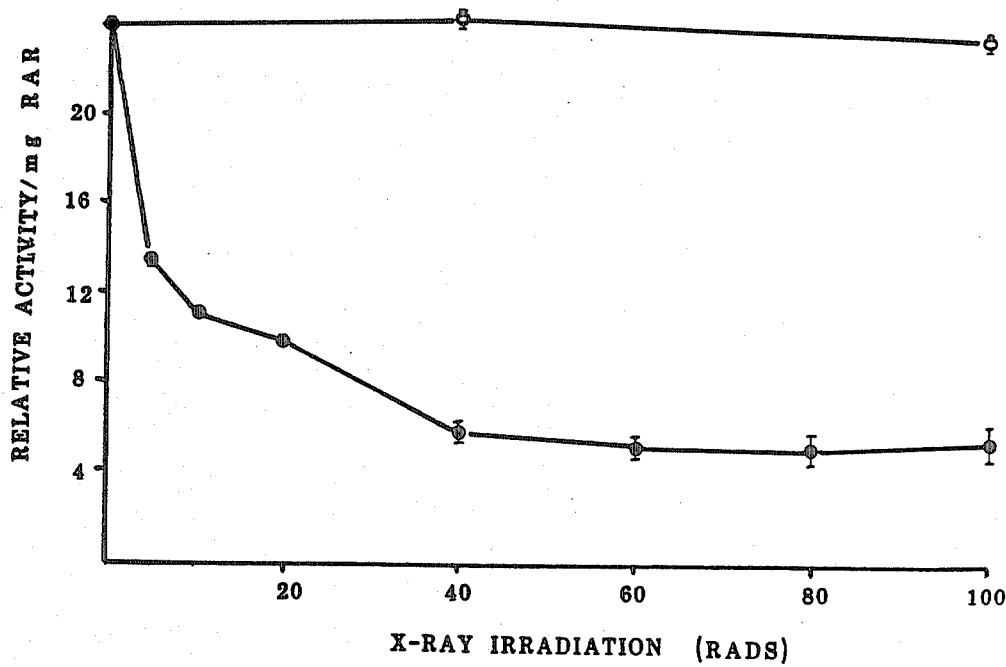

When a mixture of Asub-Q and rat lens extract is irradiated with X-rays followed by chromatographic removal of small molecules, it is found that aldose reductase is extensively irreversibly inhibited. X-ray irradiation was performed with a General Electric Maximum-100 type X-ray machine using the following settings: 100 kVp, 5 ma, 3 mm Al added, HUL=2.6 mm Al, calibrated output=175 R/min. at 15 cm. Two ml of solution with components at the same concentrations used in photolysis experiments were X-rayed in 50 mm diameter open petri dishes placed at 15.9 cm from the X-ray source. The dosages were varied from 5 to 100 Rads, requiring 1, 2, 3, 4, 34 and 51 seconds exposure, respectively. Typical results of duplicate samples recorded in Table 1 and plotted in FIG. 8 show that at 20 Rads irradiation or above the enzyme has lost approximately two thirds of its activity.

TABLE 1

X-RAY INDUCED IRREVERSIBLE INHIBITION OF ALDOSE REDUCTASE BY ASUB-Q

| System | Rads | Relative Activities |
|---|---|---|
| (Enzyme + Asub-Q)* | 5 | 30, 30 |
| (Enzyme + Asub-Q)* | 10 | 26, 23 |
| (Enzyme + Asub-Q)* | 20 | 16, 19 |
| (Enzyme + Asub-Q)* | 50 | 11, 11 |
| (Enzyme + Asub-Q)* | 100 | 11, 13 |
| Enzyme* + Asub-Q | 100 | 40, 32 |
| Enzyme + Asub-Q* | 100 | 38, 42 |
| Enzyme* + Asub-Q* | 100 | 41, 43 |
| Enzyme + Asub-Q | | 40, 46 |
| Enzyme* | 100 | 41, 43 |
| Enzyme | | 42, 45 |

*Irradiated components are indicated by asterisk with the parenthesis showing which components were irradiated after mixing.

Figure 9:
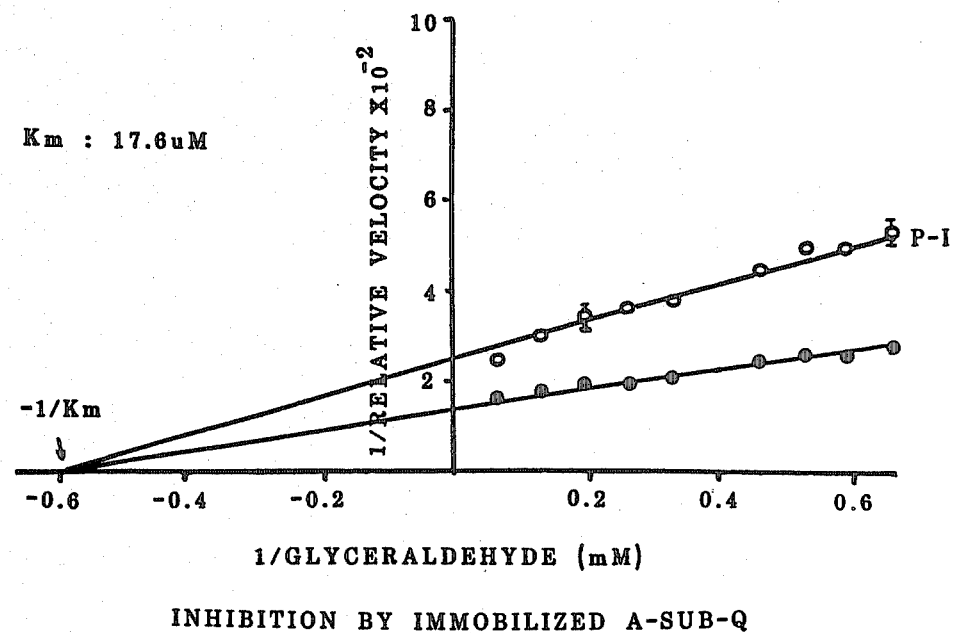

(d) REVERSIBLE INHIBITION BY SOLUBLE IMMOBILIZED ASUB-Q (1) Aldose reductase inhibition by means of the g-Globulin-NAP-Hex-quercitrin prepared in Example 2 was also investigated. The Ki and type of inhibition was established by use of a Lineweaver-Burk plot of the rate data. The results presented in FIG. 9 show that the globulin product is acting as an noncompetitive inhibitor with glyceraldehyde as the variable substrate. The assay system contains 3.75 mg/ml of the inhibitor. Since the crude lens extract consists of many proteins in addition to aldose reductase, just as the lens itself does, it is expected that the Asub-Q inhibited enzyme preparation contains inhibitor bound irreversibly to other proteins and behaves similar to the soluble immobilized g-globulin.

Figure 10:
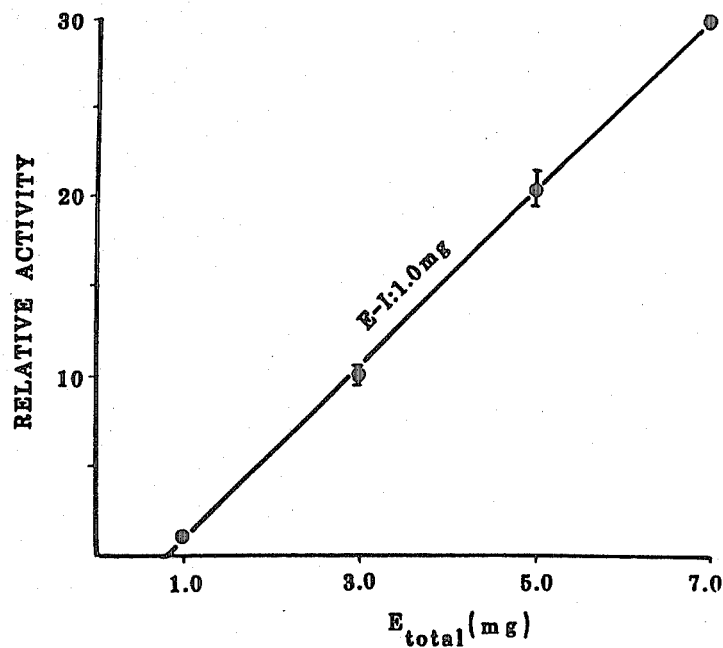
Figure 11:
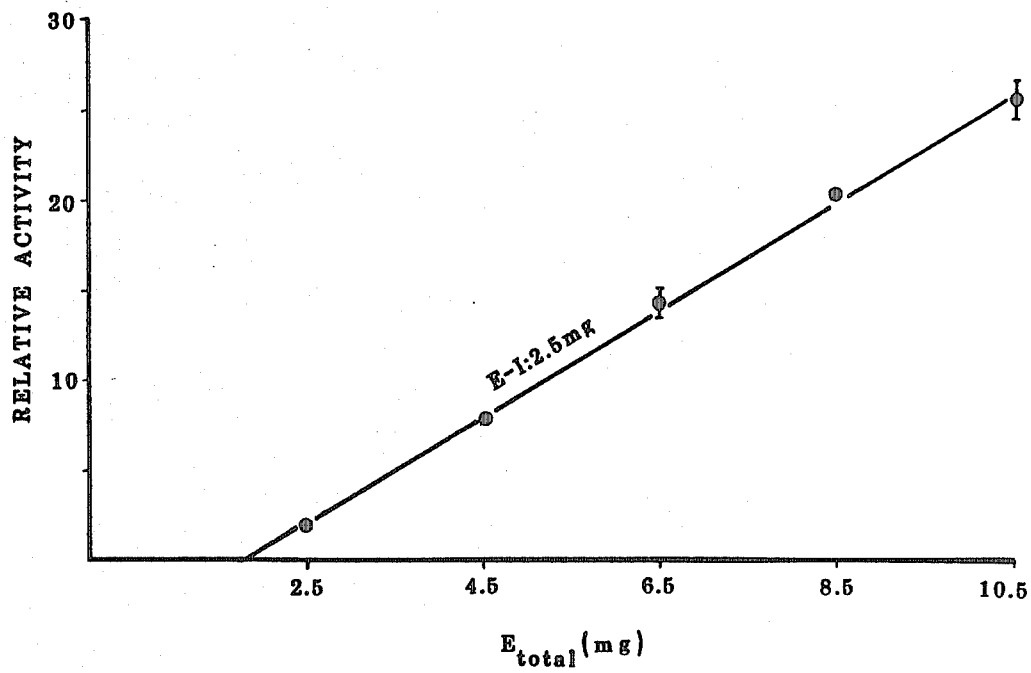

(2) If fresh aldose reductase is assayed in the presence of Asub-Q photo-inhibited aldose reductase, the fresh enzyme is inhibited reversibly by the photo-inhibited enzyme. FIG. 10 is a plot of relative enzyme activity as a function of fresh enzyme concentration when 1 mg/ml of photo-inhibited enzyme is present. FIG. 11 is similar, but 2.5 mg/ml of photo-inhibited enzyme is added in addition. The resulting decrease in slope is produced by the inhibition of fresh enzyme by photo-inhibited enzyme that is functioning as a soluble-immobilized enzyme in this system.

EXAMPLE 4

This illustrates the inhibition of cataract formation in lens organ culture by a single dose of Asub-Q irradiated with lenses.

(A) EFFECT OF ASUB-Q ON CATARACT FORMATION IN RAT LENSES IN ORGAN CULTURE EXPERIMENTS: LIGHT IRRADIATED

Organ culture was performed by a modification of the method of Kinoshita et al (see Biochem. Biophys. Acta 158, 472–475 (1968)) with a modified TC 199 medium using 50–75 gm Sprague-Dawly male rats, care being taken to avoid contamination of the system. Fresh rat lenses were treated with Asub-Q in the manner hereinafter described and incubated in the presence of fructose and in the presence of galactose, in order to determine the effect of the Asub-Q. The Asub-Q treatment involved the following:

(a) rat lenses were incubated in the dark in an incubation medium containing Asub-Q for two hours to permit the drug to diffuse into the lens;

(b) the lenses were then placed into a fresh medium and irradiated for 10 minutes for complete inhibition of aldose reductase;

(c) the lenses were then placed into a fresh medium for two hours with four changes in medium in the first 24 hours to permit non-covalently bound drug to diffuse out; and (d) the lenses were then incubated in a medium containing fructose or galactose.

In a typical experiment four groups of 20 lens, four to a Petri dish, were used. The first group was supplemented with fructose (30 mM); the second, with galactose (30 mM); the third, with fructose (30 mM) and treated with Asub-Q (0.145 mM); and the fourth, with galactose (30 mM) and treated with Asub-Q (0.145 nM). The lens were photographed with color film on a red background and evaluated on a O to V scale with O assigned to a clear lens and V to a lens with a totally opaque cataract. The procedure for treatment and photolysis of the lens was described above. The results are summarized in Table 2.

TABLE 2

EFFECT OF ASUB-Q ON RAT LENS IN ORGAN CULTURE

| Days | Fructose | Asub-Q + Fructose | Asub-Q + Galactose | Galactose |
|---|---|---|---|---|
| 0 | — | — | — | — |
| 1 | — | — | — | I(15) + II(5) |
| 2 | — | — | — | III(16) + II(4) |
| 3 | O(16) + I(4) | — | — | V(20) |
| 7 | O(16) + I(4) | O(16) + I(4) | — | |
| 10 | O(12) + I(8) | O(16) + I(4) | O(12) + I(8) | |
| 15 | O(8) + I(12) | O(12) + I(8) | O(8) + I(12) | |
| 21 | O(8) + II(8) + III(4) | O(12) + I(4) + II(4) | O(8) + I(4) + III(8) | |
| 35 | V(20) | II(8) + III(4) + V(4) | III(4) + IV(8) + V(8) | |

The number outside the parenthesis is the status of the lenses: O to V. The number inside the parenthesis is the number of the lenses.

All of the lenses with galactose supplements exhibited total cataracts after three days as previously reported by Kinoshita et al (See Biochem. Biophys. Acta 158, 472–475 (1968)). Four of the fructose containing control lenses showed very slight clouding while the remainder remained totally clear. All of the lenses containing Asub-Q remained clear. By day 21, roughly half of all the remaining lens stayed clear and half became cloudy. By day 35 all the lenses incubated with fructose were totally opaque, whereas those treated with Asub-Q were not nearly as advanced. These data indicate that lens containing Asub-Q are at least as impervious to cataract formation as control lenses that were incubated with fructose.

(B) EFFECT OF ASUB-Q ON CATARACT FORMATION IN RAT LENSES IN ORGAN CULTURE EXPERIMENTS: X-RAY IRRADIATED

This experiment was similar to the photoirradiation experiment except that the lenses were irradiated with 175 Rads of X-rays in place of light. After eight days each of the 4 control lenses incubated with fructose showed slight cataract (I) formation, as expected. Lenses incubated with galactose would be completely opaque (V). The X-ray irradiated lenses incubated with galactose were found to consist of 5 clear lenses (O) and 6 with a slight cataract (I). This experiment indicates that X-ray irradiation of Asub-Q with rat lenses results in 100% protection from sugar induced cataracts.

The foregoing shows that Asub-Q is effective as a reversible inhibitor with activity about the same as quercitrin. On irradiation, the compound functions as a photo- or X-ray sensitive irreversible affinity inhibitor for aldose reductase. The data also show that Asub-Q non-specifically forms soluble immobilized reversible inhibitor. This can potentially supplement the direct irreversible inhibition of aldose reductase in its action as an anti-diabetic cataract drug. Organ culture studies show 100% effectiveness in protecting lens from forming diabetic cataracts induced by galactose. Finally, Asub-Q serves as a good example of a new class of drugs target-directed drugs.

EXAMPLE 5

This example illustrates the inhibition of cataract formation in rats by irradiation of Asub-Q treated animals.

EFFECT OF ASUB-Q ON CATARACT FORMATION IN RATS: LIGHT IRRADIATED

Approximately 5-10 μl of Asub-Q (0.65 mM) dissolved in DMSO was injected into the aqueous humour of the right eye of each of three 75 g. rats. After 1 hour, when the drug had diffused into the lens, the rat was irradiated for 30 minutes in a Rayonet Photochemical Reactor. The rats were fed ad-libinum with a mix of 1:1 chow:galactose. The control eyes (left eye) developed detectable cataracts after 3 days. After 7 days, the cataracts in the control eyes got more extensive (III) but no cataract was observed in the treated right eyes. This was repeated on thirty rats with equivalent results.

It will be appreciated that the T-E drugs of the invention may be administered in conventional form, e.g. as tablets, capsules or pills for oral administration or as sterile solutions for intravenous administration. The composition form selected for use will depend, in large measure, on the disorder which is being treated. In the treatment of eye or ear problems, for example, topical administration may be most advantageous. The essential point is to have the composition in the form which will best center on the target site and lend itself to be irreversibly bound thereby, for example, pervasive or electromagnetic radiation such as visible light, X-rays, etc. It is particularly advantageous to have the drug irreversible receptor-binding capability activatable by light since many skin and body openings are readily accessible to light. Asub-Q is therefore especially useful as an anti-diabetic cataract drug since the eye is directly accessible to light. Other T-E drugs utilizing light as the activating energy source can similarly be prepared for use in the ears, nose, mouth and the total G.I. system as well as the skin. Additionally, if the activating sources are X-rays or other pervasive radiation, it is possible to design the T-E drug so that it can be applied to internal organs or even smaller anatomic sites in the body.

The amount of T-E drug administered will vary depending, for example, on the disorder and drug involved, mode of administration and other factors as will be understood by those in the art. Broadly speaking, however, the amount of T-E drug administered will usually fall in the range employed for the parent drug itself although, because of the improved efficiency using the T-E drug, it should be possible to reduce the effective dosages and amounts of the parent drug by as much as 25–50% or even more. In fact, a major advantage of a drug according to the invention is that the functional half-life should be much greater than that of typical drugs since its effective half-life should be dependent on neosynthesis of receptor sites, in place of the typically more rapid normal drug detoxification routes. This should allow for a much more conservative drug administration regimen such as one dose a month in place of three doses a day.

It will be appreciated that various modifications may be made in the invention as described above. Hence, the scope of the invention is defined in the following claims.

I claim:

1. A drug composition comprising three chemically joined components:
    (1) a therapeutically active drug component which acts at suitable receptor sites available for covalent bonding;
    (2) a therapeutically-acceptable component which is activatable by an external energy source selected from the group consisting of visible or ultraviolet light or X-ray to covalently bond the drug component(s) to the selected receptor site; and
    (3) a therapeutically-acceptable linking component connecting (1) and (2),
    wherein upon administration of the drug composition and exposure to said external energy source, the therapeutically active drug component is covalently bound to said receptor sites through the components (2) and (3).

2. A composition according to claim 1 wherein component (1) is an enzyme inhibitor; the linking component (3) comprises an inert polymethylene diamine chain and component (2) includes an azide group which is activatable by said external energy to covalently bind the inhibitor to a receptor site through the linking component (3).

3. A drug composition according to claim 1 which comprises a visible or ultra-violet light or X-ray activatable azide-substituted aldose reductase inhibitor.

4. A drug composition according to claim 3 which is an axide-substituted quercitrin.

5. A drug composition according to claim 4 which is N-(2-nitro-4-azidophenyl)hexylenediamine-N-(2'-O-quercitrin).

6. A pharmaceutical composition in dosage unit form comprising an effective amount of a compound according to claim 1, and a pharmaceutically-acceptable carrier.

* * * * *